United States Patent
Lai et al.

(10) Patent No.: US 9,410,893 B2
(45) Date of Patent: Aug. 9, 2016

(54) BIO-CHIP PACKAGE WITH WAVEGUIDE INTEGRATED SPECTROMETER

(71) Applicant: TAIWAN SEMICONDUCTOR MANUFACTURING COMPANY, LTD., Hsinchu (TW)

(72) Inventors: Jui Hsieh Lai, Taoyuan (TW); Ying-Hao Kuo, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 179 days.

(21) Appl. No.: 14/087,010

(22) Filed: Nov. 22, 2013

(65) Prior Publication Data
US 2015/0146203 A1    May 28, 2015

(51) Int. Cl.
*G01N 21/77* (2006.01)
*G01N 21/03* (2006.01)

(52) U.S. Cl.
CPC .... *G01N 21/7746* (2013.01); *G01N 2021/0346* (2013.01); *G01N 2021/7789* (2013.01)

(58) Field of Classification Search
CPC .............. G01N 2021/0346; G01N 2021/7789; G01N 21/7746
See application file for complete search history.

(56) References Cited

U.S. PATENT DOCUMENTS

| | | | | |
|---|---|---|---|---|
| 6,483,096 B1* | 11/2002 | Kunz | | G01N 21/6428 250/214 R |
| 7,146,074 B2* | 12/2006 | Zheng | | G01B 6/42 385/12 |
| 7,768,650 B2* | 8/2010 | Bazylenko | | G01N 21/253 356/491 |
| 2010/0055666 A1* | 3/2010 | Wimberger-Friedl | | G01N 21/6454 435/4 |
| 2010/0111771 A1* | 5/2010 | Gjerde | | G01N 1/34 422/400 |
| 2010/0255589 A1* | 10/2010 | Saiki | | G01N 33/02 436/45 |
| 2013/0309135 A1* | 11/2013 | Park | | G01N 21/17 422/69 |

OTHER PUBLICATIONS

Office Action dated Aug. 12, 2015 from corresponding application No. TW 103128047.

* cited by examiner

*Primary Examiner* — Kara E Geisel
*Assistant Examiner* — Shawn Decenzo
(74) *Attorney, Agent, or Firm* — Slater Matsil, LLP

(57) ABSTRACT

A bio-chip package comprises a substrate a first layer over the substrate comprising an image sensor. The bio-chip package also comprises a second layer over the first layer. The second layer comprises a waveguide system a grating coupler. The bio-chip package also comprises a third layer arranged to accommodate a fluid between a first-third layer portion and a second-third layer portion, and to allow the fluid to pass from a first side of the third layer to a second side of the third layer. The third layer comprises a material having a predetermined transparency with respect to a wavelength of a received source light, the waveguide system is configured to direct the received source light to the grating coupler, and the image sensor is configured to determine a change in the wavelength of the source light caused by a coupling between the source light and the fluid.

20 Claims, 6 Drawing Sheets

BIO-CHIP PACKAGE WITH WAVEGUIDE INTEGRATED SPECTROMETER

BACKGROUND

Device optical biosensors capable of detecting molecules have become useful for the biological sciences to characterize molecules such as proteins, DNA, viruses, toxins, and the like. Some molecular characterization methods employ a discrete bio-reagent, an optical fiber and spectrum system, and a dispensing system. Using optical resonances in a dielectric microparticle, also known as a whispering gallery mode (WGM), as the physical transducing mechanism is a common approach for characterizing molecules.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry various features may not be drawn to scale and are used for illustration purposes only. In fact, the dimensions of the various features in the drawings may be arbitrarily increased or reduced for clarity of discussion. One or more embodiments are illustrated in the accompanying drawings, incorporated by reference herein in their entirety, in which.

DETAILED DESCRIPTION

The following disclosure provides many different embodiments, or examples, for implementing different features of the invention. Specific examples of components and arrangements are described below to simplify the present disclosure. These are examples and are not intended to be limiting.

Optical biosensors capable of detecting and characterizing molecules have become valuable tools in the biological sciences, as well as in drug discovery. Optical biosensors commonly comprise a plurality of discrete systems.

Some optical biosensors use optical resonances in a transparent dielectric microparticle to characterize or detect molecules. The optical resonances are generated when source light, confined by total internal reflection, orbits near the particle surface and returns in phase after each revolution. The frequencies of these whispering gallery modes (WGMs), characterized by the number of wavelengths within an orbit, are extremely sensitive to added dielectric material on the microparticle surface. An atomic thickness causes a detectable shift of a given resonance frequency or wavelength of the source light received by the optical biosensor. A distributed feedback laser diode with a nominal wavelength is often used as a tunable laser light source. Optical resonances of the microparticles that are detected as dips or changes in the transmitted intensity as a function of laser wavelength are determined. A resonance will shift to a longer wavelength to accommodate a larger circumference of a particle, for example.

Because common optical biosensors include a plurality of discrete systems, common optical biosensors are often large, complicated, prone to error, and time consuming to use. Further, common molecular characterization methods often use a reagent with a fluorescence reactant to quantify the molecules. Reliance on such a fluorescence reactant for characterizing molecules can lead to inaccurate results.

Accordingly, in some embodiments, an optical biosensor has a compact size, reduces the complexities involved with molecular characterization, and improves accuracy and reliability.

Figure 1A:
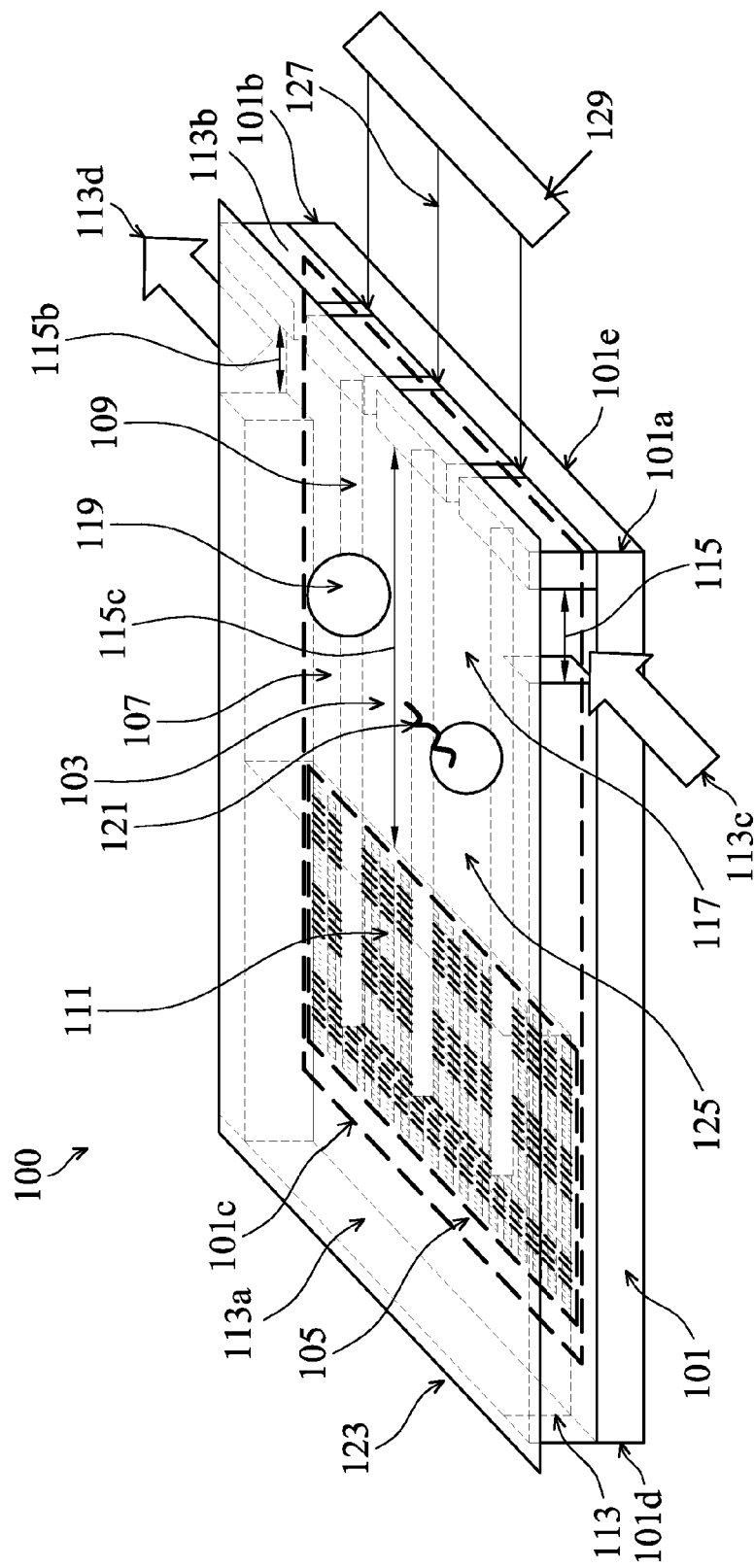
FIG. 1A is an isometric view of a bio-chip package with an integrated optical spectrometer, in accordance with one or more embodiments.

FIG. 1A is an isometric view of a bio-chip package 100 with an integrated optical spectrometer for characterizing one or more molecules, in accordance with one or more embodiments. The bio-chip package 100 is configured to provide a capillary function for the bio-chip package, and instead of using a fluorescence reactance, the bio-chip package uses more sensitive WGM to characterize molecules. The bio-chip package 100 is compact, has a low profile, and uses only a small sample volume of fluid having the molecule(s) to be characterized. The low profile and small volume makes it possible to save time and money because less fluid is used in a molecular characterization method compared to conventional methods, and multiple discrete systems need not be setup.

The bio-chip package 100 comprises a substrate 101 having a first side 101a and a second side 101b opposite the first side 101a. The substrate 101 comprises combination of Si, SiGe, polymer material, or other suitable material.

The bio-chip package 100 also comprises a first layer 103 over the substrate 101 covering a first-substrate portion 101c. The first layer 103 comprises an image sensor 105. The bio-chip package 100 further comprises a second layer 107 over the first layer 103 and at least some of the first-substrate portion 101c. The second layer comprises a waveguide system 109 and a grating coupler 111.

Figure 1B:
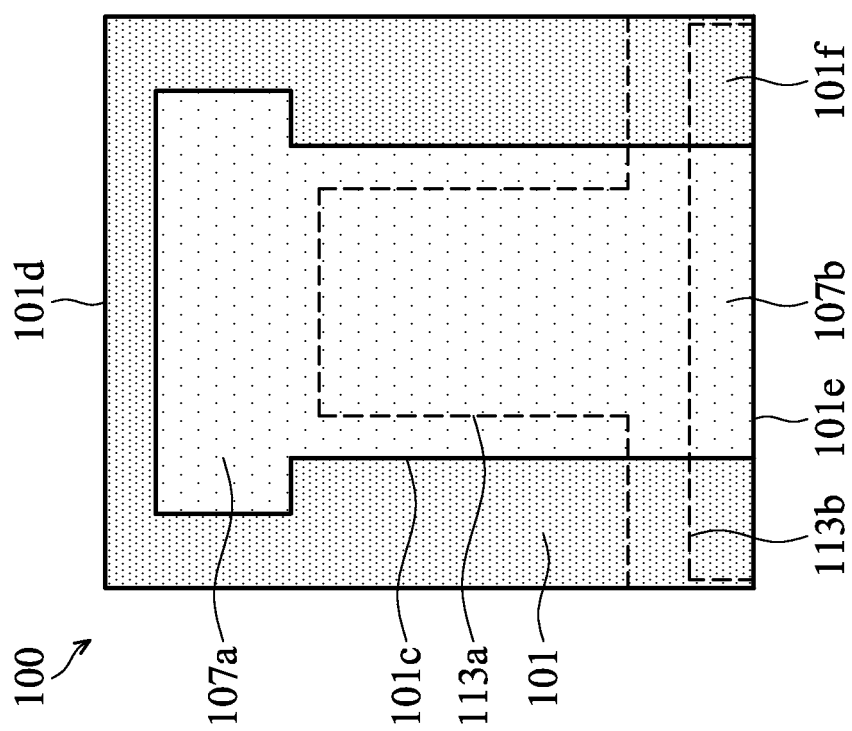
FIG. 1B is a top-side schematic view of a bio-chip package with an integrated optical spectrometer, in accordance with one or more embodiments.

The bio-chip package 100 additionally comprises a third layer 113. The third layer 113 is a dam layer that comprises a first-third layer portion 113a over a first-second layer portion 107a (FIG. 1B). The first-second layer portion 107a and the first-third layer portion 113a are toward a third side 101d of the substrate 101. The first-second layer portion 107a comprises some of the waveguide system 109.

The third layer 113 further comprises a second-third layer portion 113b over a second-second layer portion 107b (FIG. 1B). The second-second layer portion 107b is toward a fourth side 101e of the substrate 101. The second-second layer portion 107a comprises the grating coupler 111 and overlies the image sensor 105. Accordingly, the second-third layer portion 113a at least covers the grating coupler 111 and the image sensor 105.

The second-third layer portion 113b is also over at least some of the first-substrate portion 101c and a second-substrate portion 101f (FIG. 1B) excluded from the first-substrate portion 101c. The first-third layer portion 113a is separated from the second-third layer portion 113b by a spacing 115. The first-third layer portion 113a and the second-third layer portion 113b are arranged such that the third layer 113 accommodates a fluid 117 between the first-third layer portion 113a and the second-third layer portion 113b. The fluid 117 is a bio-catalytic reagent or a bio-affinity reagent. In some embodiments, the fluid 117 optionally includes a transparent dielectric or molecular microspheres 119 and/or molecules 121 that comprise a combination of proteins, viruses, bacteria, toxins, and the like, to be characterized using the bio-chip package 100.

The first-third layer portion 113a and the second-third layer portion 113b are configured to allow the fluid 117 to pass from a first side of the third layer 113c over the first side of the substrate 101a to a second side of the third layer 113d over the second side of the substrate 101b. In some embodiments, the first-third layer portion 113a and the second-third layer portion 113b are separated by the spacing 115 such that fluid passes from the first side of the third layer 113c to the second side of the third layer 113d by way of capillary action.

The bio-chip package 100 also comprises a fourth layer 123 over the third layer 113, the spacing 115 between the first-third layer portion 113a, and the second-third layer portion 113b. The fourth layer 123, the third layer 113, and the second layer 107 together form a cavity 125 within which the fluid 117 is accommodated.

In some embodiments, the third layer 113 comprises a material having a predetermined transparency with respect to a wavelength of a received source light 127. The waveguide system 109 is configured to direct the received source light 127 to the grating coupler 111. The image sensor 105 is configured to determine a change in the wavelength of the source light 127 caused by a coupling between the source light 127 and the fluid 117, including the molecular microsphere 119 and/or the molecules 121 of or in the fluid 117.

In some embodiments, the first-third layer portion 113a and the second-third layer portion 113b are arranged to cause the fluid 117 to pass from the first side of the third layer 113c to the second side of the third layer 113d by capillary action into and out of the cavity 125. In order to facilitate the capillary action in some embodiments, the spacing 115 between the first-third layer portion 113a and the second-third layer portion 113b on the first side of the third layer 113c ranges from about 100 micrometers to about 1000 micrometers, and the spacing 115b between the first-third layer portion 113a and the second-third layer portion 113b on the second side of the third layer 113d ranges from about 100 micrometers to about 1000 micrometers. In some embodiments, the spacing 115 and the spacing 115b are equal or about equal. In other embodiments, the spacing 115 and the spacing 115b are different to effect flow of the fluid 117 into and out of the cavity 125.

In some embodiments, the first-third layer portion 113a and the second-third layer portion 113b are arranged such that a spacing 115c between the first-third layer portion 113a and the second-third layer portion 113b that is between the first side of the third layer 113c and the second side of the third layer 113d is greater than the spacing 115 between the first-third layer portion 113a and the second-third layer portion 113b on the first side of the third layer 113c and the spacing 115b between the first-third layer portion 113a and the second-third layer portion 113b on the second side of the third layer 113d.

In some embodiments, the source light 127 is input into the waveguide system 109 by an external light source 129 such as, but not limited to, a laser diode. In one or more embodiments, the light source 129 is tunable to provide source light 127 at a wavelength ranging from about 400 nm to about 2000 nm.

FIG. 1B is a top-side schematic view of the bio-chip package 100, in accordance with one or more embodiments. The third layer 113 (FIG. 1A) comprises the first-third layer portion 113a over the first-second layer portion 107a. The first-second layer portion 107a and the first-third layer portion 113a are toward the third side 101d of the substrate 101. The first-second layer portion 107a comprises some of the waveguide system 109 (FIG. 1A).

The third layer 113 further comprises the second-third layer portion 113b over the second-second layer portion 107b. The second-second layer portion 107b is toward the fourth side 101e of the substrate 101. The second-second layer portion 107b comprises the grating coupler 111 (FIG. 1A) and overlies the image sensor 105 (FIG. 1A). Accordingly, the second-third layer portion 113b at least covers the grating coupler 111 and the image sensor 105.

The second-third layer portion 113b is also over at least some of the first-substrate portion 101c and the second-substrate portion 101f excluded from the first-substrate portion 101c.

Figure 2:
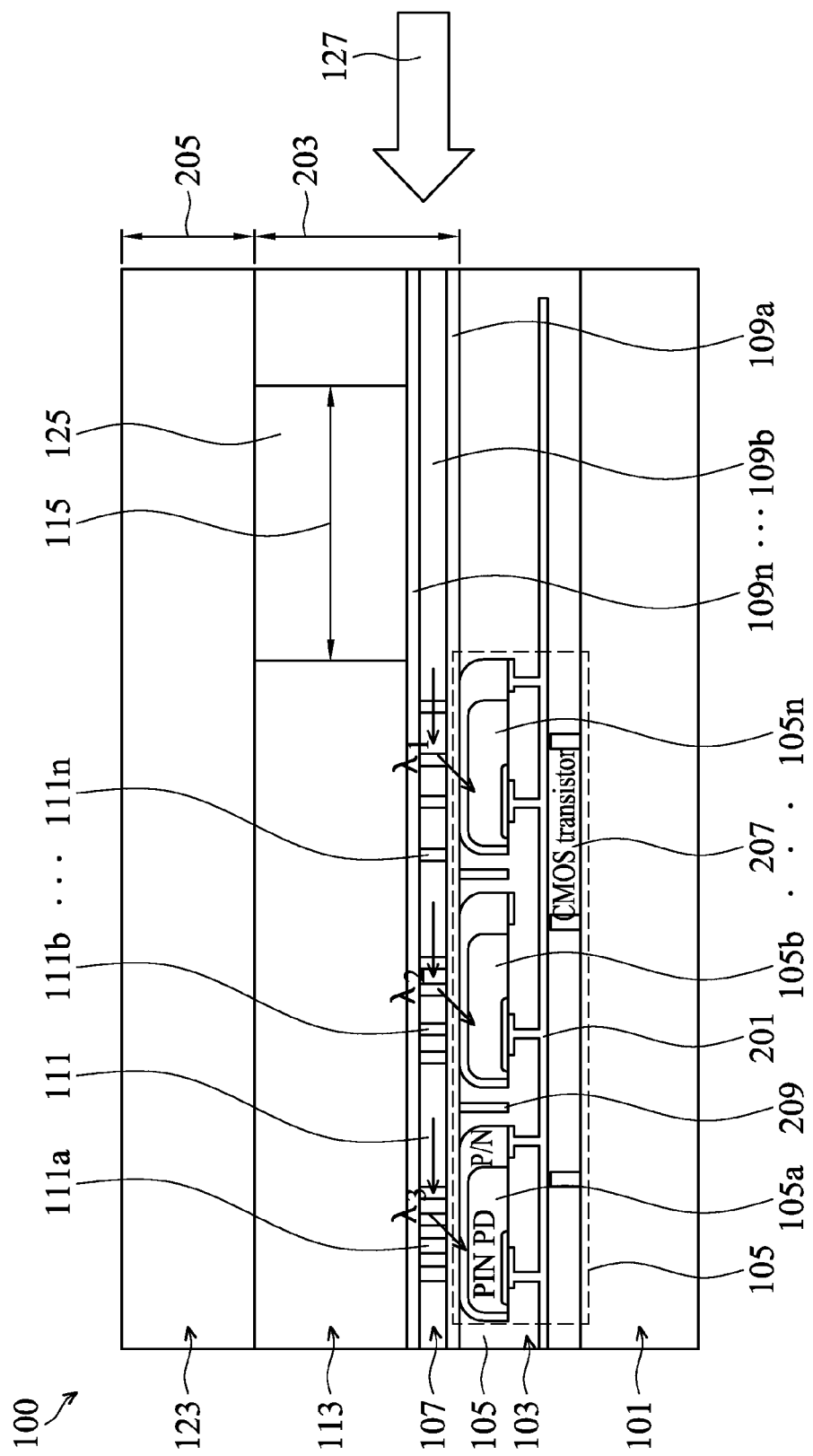
FIG. 2 is a cross-sectional side view of a bio-chip package, in accordance with one or more embodiments.

FIG. 2 is a cross-sectional side view of the bio-chip package 100, in accordance with one or more embodiments. The first layer 103 is over the substrate 101. The second layer 107 is over the first layer 103. The third layer 113 is over the first-second layer portion 107a and the second-second layer portion 107b (i.e., at least over the grating coupler 111 and the image sensor 105), leaving the spacing 115 between the first-third layer portion 113a and the second-third layer portion 113b. The fourth layer 123 is over the third layer 113, the second layer 107, and the cavity 125.

The bio-chip package 100 additionally includes a connector 201. The connector 201, for example, is a redistribution layer that couples the image sensor 105 to other layers of the bio-chip package 100 and/or a processor configured to characterize a molecule of or in the fluid 117, such as molecular microsphere 119 and/or molecule 121. The connector 201 comprises one or more conductive materials comprising a combination of copper, aluminum, gold, or any other suitable material.

In some embodiments, the third layer 113 is configured to be transparent with respect to one or more predetermined wavelengths. In some embodiments, the third layer 113 is configured to be opaque with respect to one or more predetermined wavelengths of the source light 127. In some embodiments, the third layer 113 comprises any of a glass, a polymer, or other suitable material.

In some embodiments, the third layer 113 has a height 203 with respect to the second layer 107 ranging from about 100 micrometers to about 1000 micrometers. The height 203 provides a low profile and compact size for the bio-chip package 100. In some embodiments, the fourth layer 123 comprises a transparent or translucent material such as glass or other suitable material. In some embodiments, the fourth layer 123 has a thickness 205 ranging from about 300 micrometers to about 500 micrometers. The thickness 205 for the fourth layer 123 also provides a bio-chip package 100 having a low profile and compact size.

In some embodiments, the grating coupler 111 comprises a one or more sections 111a-111n having a grating pitch configured to direct received source light 127 of a corresponding wavelength λ to the image sensor 105. In some embodiments, the one or more sections 111a-111n comprise a plurality of sections 111a-111n. Each of the plurality of sections 111a-111n has a grating pitch that is different than the other sections of the plurality of sections 111a-111n. Each section of the plurality of sections 111a-111n is thereby being configured to direct received source light 127 to a corresponding image sensor portion 105a-105n of the image sensor 105 based on the wavelength λ of the source light 127 received by the grating coupler 111. In some embodiments, the grating pitch of the one or more sections 111a-111n ranges from about 100 nm to about 1000 nm, depending on a wavelength λ preselected to be diverted into a specific sensor portion 105a-105n. In some embodiments, the grating coupler comprises one or more reflective and/or conductive materials comprising a combination of copper, aluminum, or any other suitable material.

In some embodiments, the waveguide system 109 comprises one or more layers 109a-109n. The one or more layers 109a-109n of the waveguide system 109 comprise, for example, a bottom clad layer 109a, a core clad layer 109b, and an upper clad layer 109n. The upper clad layer 109n and/or the lower clad layer 109a are passivation layers that comprise one or more of SiO2, a polymer material, or other suitable material. The core clad layer 109b is a passivation layer that comprises any combination of PBO, a polymer material, SiNx, or other suitable material.

In some embodiments, the image sensor 105 comprises a CMOS transistor 207. In some embodiments, the first layer 103 also comprises one or more of a low-k material or a low-k polymer material within which the image sensor 105, the connector 201 and/or the CMOS transistor 207 reside. In one or more embodiments, the image sensor portions 105a-105n comprise various combinations of n-doped and p-doped regions in the first layer 103. The image sensor portions 105a-105n are separated by a plurality of isolation features 209 between each image sensor portion 105a-105n. The isolation features 209 are configured to prevent coupling between the image sensor portions 105a-105n. Accordingly, the connector 201 is also configured to couple the image sensor portions 105a-105n to the CMOS transistor 207. In some embodiments, the connector 201 is configured to couple the image sensor 105 to a processor such as processor 503, discussed below. The image sensor 105 and the processor 503 are together configured to characterize one or more molecular microspheres 119 and/or one or more molecules 121 in the fluid 117 based, at least in part, on data collected by the image sensor 105 such as a determination that light is received by a particular image sensor portion 105a-105n.

Figure 3:
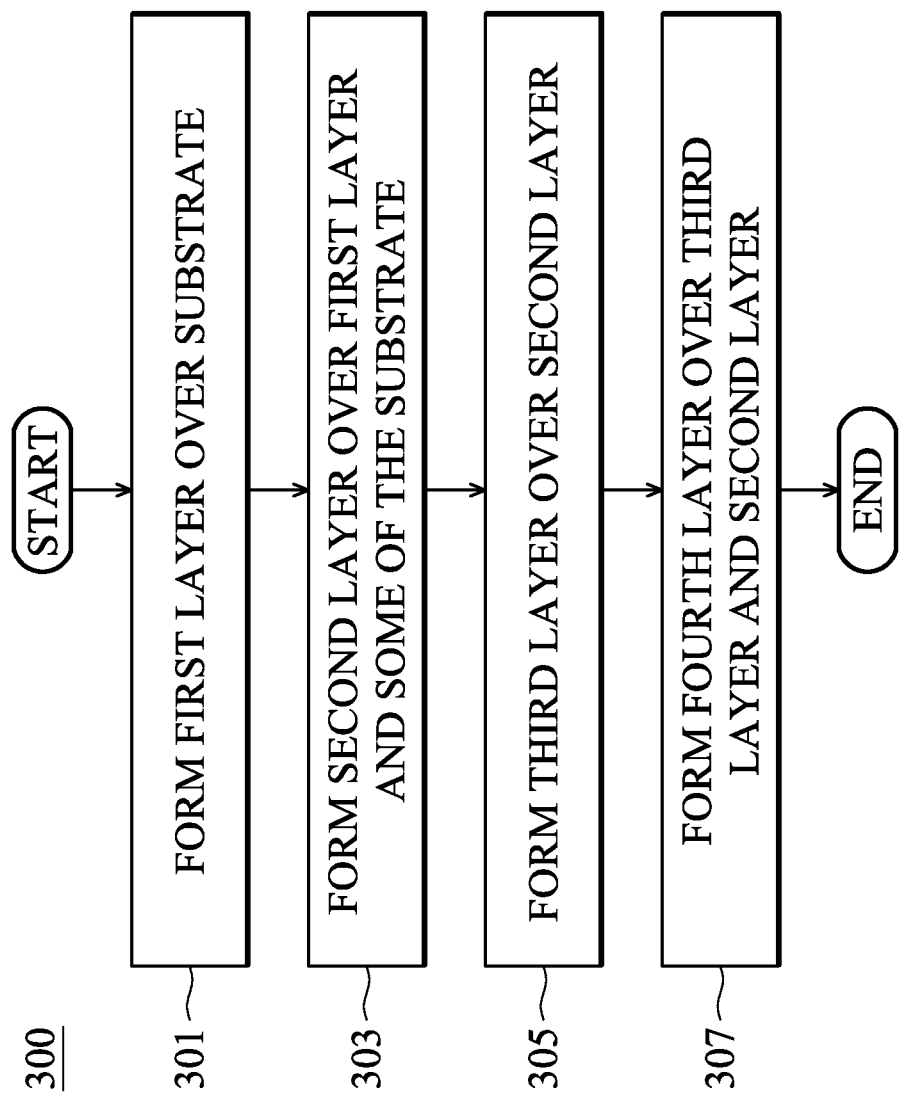
FIG. 3 is a flow chart of a method forming a bio-chip package, in accordance with one or more embodiments.

FIG. 3 is a flow chart of a method 300 of forming a bio-chip package, in accordance with one or more embodiments. Method 300 begins with operation 301 in which a first layer is formed over a substrate. The substrate has a first side and a second side opposite the first side, and the first layer is formed to cover a first-substrate portion. The first layer comprises an image sensor.

In operation 303, a second layer is formed over the first layer and at least some of the first-substrate portion. The second layer comprises a waveguide system and a grating coupler.

In operation 305, a third layer is formed such that a first-third layer portion is formed over a first-second layer portion, and a second-third layer portion is formed over a second-second layer portion, at least some of the first-substrate portion, and a second-substrate portion excluded from the first-substrate portion. In some embodiments, the third layer is formed entirely over the second layer and a portion of the third layer is removed by, for example, an etching process, photolithography process, and dispensing process, or other suitable process, leaving the first-third layer portion and the second-third layer portion such that the first-third layer portion being separated from the second-third layer portion by a spacing. In other embodiments the first-third layer portion and the second-third layer portion are selectively formed using any suitable process for forming a layer in a bio-chip package on the second layer such that the such that the first-third layer portion being separated from the second-third layer portion by a spacing.

In operation 307, a fourth layer is formed over the third layer and the spacing between the first-third layer portion and the second-third layer portion. The fourth layer, the third layer, and the second layer together form a cavity configured to accommodate a fluid.

Figure 4:
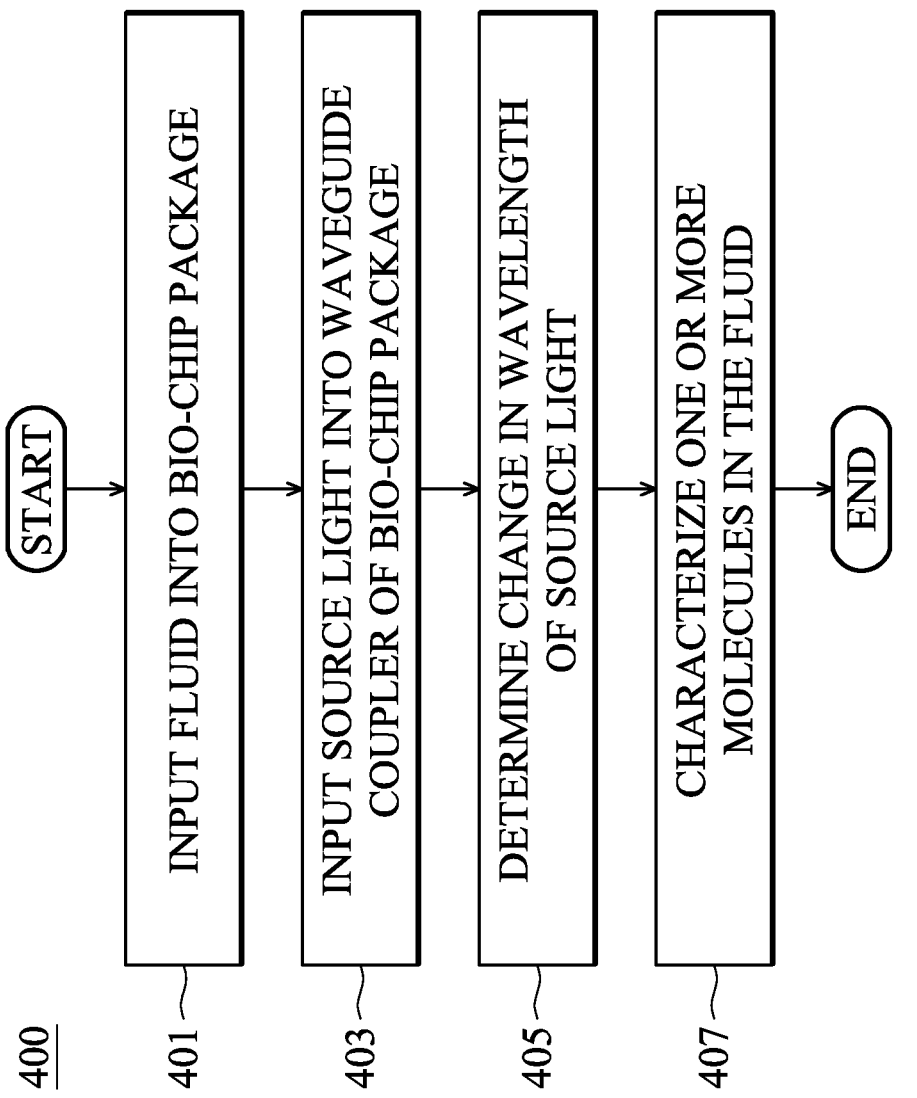
FIG. 4 is a flow chart of a method of characterizing one or more molecules in a fluid, in accordance with one or more embodiments.

FIG. 4 is a flow chart of a method 400 of characterizing one or more molecules in a fluid, in accordance with one or more embodiments. Method 400 begins with operation 401 by inputting a fluid by capillary action into a bio-chip package. In operation 403, a source light is input into a waveguide coupler of the bio-chip package. The source light has a predetermined wavelength.

In operation 405, a change in the wavelength of the source light is determined based, at least in part, on feedback from an image sensor of the bio-chip package communicated to a processor coupled to the bio-chip package by a connector of the bio-chip package.

In operation 407, one or more molecules in the fluid in a cavity of the bio-chip package are characterized based, at least in part, on the determined change in the wavelength of the source light caused by a coupling effect between the source light and the fluid.

The processes described herein for characterizing one or more molecules in a fluid may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 5:
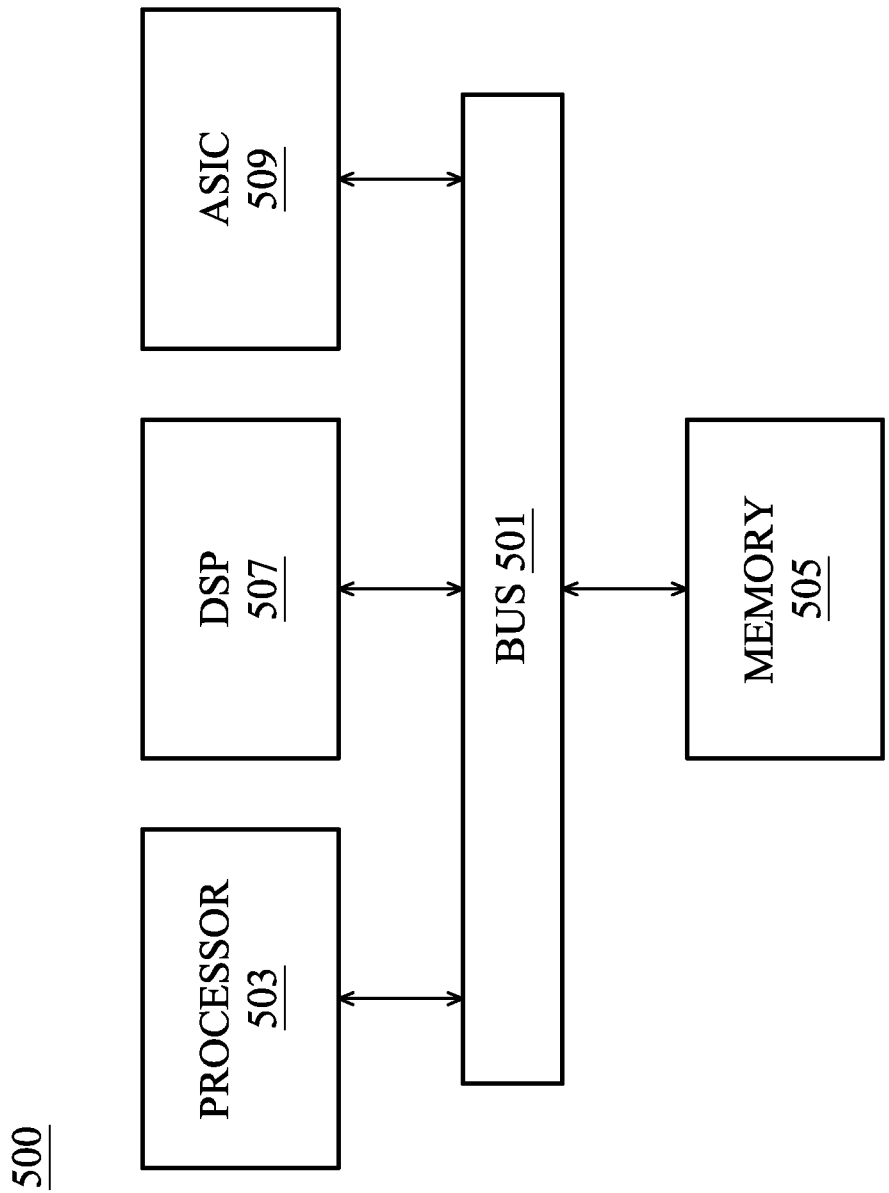
FIG. 5 illustrates a chip set or chip upon which or by which an embodiment is implemented.

FIG. 5 illustrates a chip set or chip 500 upon which or by which an embodiment is implemented. Chip set 500 is programmed to characterize one or more molecules in a fluid, as described herein, and includes, for example, bus 501, processor 503, memory 505, DSP 507 and ASIC 509 components.

The processor 503 and memory 505 are incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. In some embodiments, the chip set 500 are implemented in a single chip. In some embodiments the chip set or chip 500 is implemented as a single "system on a chip." In some embodiments, a separate ASIC is not be used, for example, and that all relevant functions as disclosed herein would be performed by a processor or processors, e.g., processor 503. Chip set or chip 500, or a portion thereof, constitutes a mechanism for performing one or more steps of characterizing one or more molecules in a fluid.

In one or more embodiments, the chip set or chip 500 includes a communication mechanism such as bus 501 for passing information among the components of the chip set 500. Processor 503 has connectivity to the bus 501 to execute instructions and process information stored in, for example, the memory 505. In some embodiments, the processor 503 is also accompanied with one or more specialized components to perform certain processing functions and tasks such as one or more digital signal processors (DSP) 507, or one or more application-specific integrated circuits (ASIC) 509. A DSP 507 typically is configured to process real-world signals (e.g., sound) in real time independently of the processor 503. Similarly, an ASIC 509 is configurable to perform specialized functions not easily performed by a more general purpose processor. Other specialized components to aid in performing the functions described herein optionally include one or more field programmable gate arrays (FPGA), one or more controllers, or one or more other special-purpose computer chips.

In one or more embodiments, the processor (or multiple processors) 503 performs a set of operations on information as specified by computer program code related to characterizing one or more molecules in a fluid. The computer program code is a set of instructions or statements providing instructions for the operation of the processor and/or the computer system to perform specified functions.

The processor 503 and accompanying components have connectivity to the memory 505 via the bus 501. The memory 505 includes one or more of dynamic memory (e.g., RAM, magnetic disk, writable optical disk, etc.) and static memory (e.g., ROM, CD-ROM, etc.) for storing executable instructions that when executed perform the operations described herein to characterize one or more molecules in a fluid. The memory 505 also stores the data associated with or generated by the execution of the operations.

In one or more embodiments, the memory 505, such as a random access memory (RAM) or any other dynamic storage device, stores information including processor instructions for characterizing one or more molecules in a fluid. Dynamic memory allows information stored therein to be changed by system 100. RAM allows a unit of information stored at a location called a memory address to be stored and retrieved independently of information at neighboring addresses. The memory 505 is also used by the processor 503 to store temporary values during execution of processor instructions. In various embodiments, the memory 505 is a read only memory (ROM) or any other static storage device coupled to the bus 501 for storing static information, including instructions, that is not changed by the system 100. Some memory is composed of volatile storage that loses the information stored thereon when power is lost. In some embodiments, the memory 505 is a non-volatile (persistent) storage device, such as a magnetic disk, optical disk or flash card, for storing information, including instructions, that persists even when the system 100 is turned off or otherwise loses power.

The term "computer-readable medium" as used herein refers to any medium that participates in providing information to processor 503, including instructions for execution. Such a medium takes many forms, including, but not limited to computer-readable storage medium (e.g., non-volatile media, volatile media). Non-volatile media includes, for example, optical or magnetic disks. Volatile media include, for example, dynamic memory. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, or another medium from which a computer can read. The term computer-readable storage medium is used herein to refer to a computer-readable medium.

One aspect of this description relates to a bio-chip package that comprises a substrate having a first side and a second side opposite the first side and a first layer over the substrate covering a first-substrate portion. The first layer comprises an image sensor. The bio-chip package also comprises a second layer over the first layer and at least some of the first-substrate portion. The second layer comprises a waveguide system and a grating coupler. The bio-chip package further comprises a third layer. The third layer comprises a first-third layer portion over a first-second layer portion, and a second-third layer portion over a second-second layer portion, at least some of the first-substrate portion, and a second-substrate portion excluded from the first-substrate portion. The first-third layer portion is separated from the second-third layer portion by a spacing such that the third layer is arranged to accommodate a fluid between the first-third layer portion and the second-third layer portion, and to allow the fluid to pass from a first side of the third layer over the first side of the substrate to a second side of the third layer over the second side of the substrate. The bio-chip package additionally comprises a fourth layer over the third layer and the spacing between the first-third layer portion and the second-third layer portion. The fourth layer, the third layer, and the second layer together forming a cavity therebetween within which the fluid is accommodated. The third layer comprises a material having a predetermined transparency with respect to a wavelength of a received source light. The waveguide system is configured to direct the received source light to the grating coupler. The image sensor is configured to determine a change in the wavelength of the source light caused by a coupling between the source light and the fluid.

Another aspect of this description relates to a method comprising forming a first layer over a substrate having a first side and a second side opposite the first side, the first layer covering a first-substrate portion, the first layer comprising an image sensor. The method also comprises forming a second layer over the first layer and at least some of the first-substrate portion, the second layer comprising a waveguide system, and a grating coupler. The method further comprises forming a third layer comprising a first-third layer portion over a first-second layer portion, and a second-third layer portion over a second-second layer portion, at least some of the first-substrate portion, and a second-substrate portion excluded from the first-substrate portion, the first-third layer portion being separated from the second-third layer portion by a spacing, such that the third layer is arranged to accommodate a fluid between the first-third layer portion and the second-third layer portion, and to allow the fluid to pass from a first side of the third layer over the first side of the substrate to a second side of the third layer over the second side of the substrate. The method additionally comprises forming a fourth layer over the third layer and the spacing between the first-third layer portion and the second-third layer portion, the fourth layer, the third layer, and the second layer together forming a cavity therebetween within which the fluid is accommodated. The third layer comprises a material having a predetermined transparency with respect to a wavelength of a received source light, the waveguide system is configured to direct the received source light to the grating coupler, and the image sensor is configured to determine a change in the wavelength of the source light caused by a coupling between the source light and the fluid.

Still another aspect of this description relates to a method comprising inputting a fluid by capillary action into a bio-chip package comprising a substrate, a first layer over the substrate, an image sensor in the first layer, a second layer over the first layer and at least some of the first-substrate portion, a waveguide system in the second layer, a grating coupler in the second layer, a third layer comprising a first-third layer portion over a first-second layer portion, and a second-third layer portion over a second-second layer portion, at least some of the first-substrate portion, and a second-substrate portion excluded from the first-substrate portion, the first-third layer portion being separated from the second-third layer portion by a spacing, such that the third layer is arranged to accommodate the fluid between the first-third layer portion and the second-third layer portion, and to allow the fluid to pass from a first side of the third layer over a first side of the substrate to a second side of the third layer over a second side of the substrate. The method also comprises inputting a source light having a wavelength into the waveguide coupler. The method further comprises characterizing one or more molecules in the fluid in the cavity based, at least in part, on a change in the wavelength of the source light caused by a coupling effect between the source light and the fluid.

It will be readily seen by one of ordinary skill in the art that the disclosed embodiments fulfill one or more of the advantages set forth above. After reading the foregoing specification, one of ordinary skill will be able to affect various changes, substitutions of equivalents and various other embodiments as broadly disclosed herein. Although features of various embodiments are expressed in certain combinations among the claims, it is contemplated that these features can be arranged in any combination and order. It is therefore intended that the protection granted hereon be limited only by the definition contained in the appended claims and equivalents thereof.

What is claimed is:

1. A bio-chip package comprising:
a substrate having a first side and a second side opposite the first side;
a first layer over the substrate covering a first-substrate portion, the first layer comprising an image sensor;
a second layer over the first layer and at least some of the first-substrate portion, the second layer comprising
a waveguide system; and
a grating coupler;
a third layer comprising
a first-third layer portion over a first-second layer portion; and
a second-third layer portion over a second-second layer portion, at least some of the first-substrate portion, and a second-substrate portion excluded from the first-substrate portion, the first-third layer portion being separated from the second-third layer portion by a spacing, such that the third layer is arranged to accommodate a fluid between the first-third layer portion and the second-third layer portion, and to allow the fluid to pass from a first side of the third layer over the first side of the substrate to a second side of the third layer over the second side of the substrate; and
a fourth layer over the third layer and the spacing between the first-third layer portion and the second-third layer portion, the fourth layer, the third layer, and the second layer together forming a cavity therebetween within which the fluid is accommodated,
wherein the third layer comprises a material having a predetermined transparency with respect to a wavelength of a received source light, the waveguide system being configured to direct the received source light to the grating coupler, and the image sensor being configured to determine a change in the wavelength of the source light caused by a coupling between the source light and the fluid.

2. The bio-chip package of claim 1, wherein the first-third layer portion and the second-third layer portion are arranged to cause the fluid to pass from the first side of the third layer to the second side of the third layer by capillary action into and out of the cavity.

3. The bio-chip package of claim 1, wherein the spacing between the first-third layer portion and the second-third layer portion on the first side of the third layer ranges from about 100 micrometers to about 1000 micrometers, and the spacing between the first-third layer portion and the second-third layer portion on the second side of the third layer ranges from about 100 micrometers to about 1000 micrometers.

4. The bio-chip package of claim 1, wherein the grating coupler comprises one or more sections having a grating pitch configured to direct received source light of a corresponding wavelength to the image sensor.

5. The bio-chip package of claim 4, wherein the one or more sections comprise a plurality of sections, each of the plurality of sections have a grating pitch different than the other sections of the plurality of sections, each section of the plurality of sections thereby being configured to direct received source light to a corresponding image sensor portion of the image sensor based on the wavelength of the source light received by the grating coupler.

6. The bio-chip package of claim 1, wherein the first-third layer portion and the second-third layer portion are arranged such that the spacing between the first-third layer portion and the second-third layer portion between the first side of the third layer and the second side of the third layer is greater than the spacing between the first-third layer portion and the second-third layer portion on the first side of the third layer and the spacing between the first-third layer portion and the second-third layer portion on the second side of the third layer.

7. The bio-chip package of claim 1, wherein the image sensor comprises a CMOS transistor.

8. The bio-chip package of claim 1, wherein the third layer has a height with respect to the second layer ranging from about 100 micrometers to about 1000 micrometers.

9. The bio-chip package of claim 1, wherein the fourth layer is glass.

10. The bio-chip package of claim 1, further comprising:
a connector configured to couple the image sensor to a processor, the image sensor and the processor being together configured to characterize one or more molecules in the fluid based, at least in part, on data collected by the image sensor.

11. A method of making a bio-chip package comprising:
forming a first layer over a substrate having a first side and a second side opposite the first side, the first layer covering a first-substrate portion, the first layer comprising an image sensor;
forming a second layer over the first layer and at least some of the first substrate portion, the second layer comprising
a waveguide system; and
a grating coupler;
forming a third layer comprising a first-third layer portion over a first-second layer portion, and a second-third layer portion over a second-second layer portion, at least some of the first-substrate portion, and a second-substrate portion excluded from the first-substrate portion, the first-third layer portion being separated from the second-third layer portion by a spacing, such that the third layer is arranged to accommodate a fluid between the first-third layer portion and the second-third layer portion, and to allow the fluid to pass from a first side of the third layer over the first side of the substrate to a second side of the third layer over the second side of the substrate; and
after forming the third layer, forming a fourth layer over the third layer and the spacing between the first-third layer portion and the second-third layer portion, the fourth layer, the third layer, and the second layer together forming a cavity therebetween within which the fluid is accommodated, wherein the third layer comprises a material having a predetermined transparency with respect to a wavelength of a received source light, the waveguide system being configured to direct the received source light to the grating coupler, and the image sensor is configured to determine a change in the wavelength of the source light caused by a coupling between the source light and the fluid.

12. The method of claim 11, further comprising:
forming the first-third layer portion and the second-third layer portion at positions that cause the fluid to pass from the first side of the third layer to the second side of the third layer by capillary action into and out of the cavity.

13. The method of claim 11, further comprising:
forming the first-third layer portion and the second-third layer portion having a spacing between the first-third layer portion and the second-third layer portion ranging from about 100 micrometers to about 1000 micrometers on the first side of the third layer, and the spacing between the first-third layer portion and the second-third layer portion on the second side of the third layer ranging from about 100 micrometers to about 1000 micrometers.

14. The method of claim 11, wherein forming the second layer comprises forming the grating coupler to have one or more sections having a grating pitch configured to direct received source light of a corresponding wavelength to the image sensor.

15. The method of claim 14, wherein the one or more sections comprise a plurality of sections, each of the plurality of sections have a grating pitch different than the other sections of the plurality of sections, each section of the plurality of sections thereby being configured to direct received source light to a corresponding image sensor portion of the image sensor based on the wavelength of the source light received by the grating coupler.

16. The method of claim 11, wherein forming the first layer further comprises:
forming a CMOS transistor in the first layer, image sensor comprising the CMOS transistor.

17. The method of claim 11, wherein the third layer has a height with respect to the second layer ranging from about 100 micrometers to about 1000 micrometers.

18. A bio-chip package comprising:
an image sensor over a substrate;
a waveguide system over the image sensor;
a grating coupler over the image sensor;
a fluid passage over the grating coupler,
wherein
the fluid passage is defined by at least one sidewall comprising a material having a predetermined transparency with respect to a wavelength of a received source light,
the waveguide system is configured to direct the received source light to the grating coupler, and
the image sensor is configured to detect a change in the wavelength of the source light caused by a coupling between the source light and a fluid accommodated within the fluid passage.

19. The bio-chip package of claim 18, wherein the grating coupler comprises at least one section having a grating pitch configured to direct received source light of a corresponding wavelength to the image sensor.

20. The bio-chip package of claim 18, wherein the image sensor comprises a CMOS transistor.

* * * * *